United States Patent [19]
Stern et al.

[11] Patent Number: 5,226,107
[45] Date of Patent: Jul. 6, 1993

[54] APPARATUS AND METHOD OF USING FIBER-OPTIC LIGHT GUIDE FOR HEATING ENCLOSED TEST ARTICLES

[75] Inventors: Theodore G. Stern; Mickey Cornwall, both of San Diego; Donald A. Nirschl, Del Mar, all of Calif.

[73] Assignee: General Dynamics Corporation, Space Systems Division, San Diego, Calif.

[21] Appl. No.: 880,931

[22] Filed: Jun. 22, 1992

[51] Int. Cl.$^5$ .......................... A21B 2/00; F26B 19/00
[52] U.S. Cl. .................................. 392/416; 392/419; 324/96; 324/158 R
[58] Field of Search ............... 392/416, 419, 420, 421; 219/405, 411, 390; 324/96, 158 R, 158 D, 158 F

[56] References Cited

U.S. PATENT DOCUMENTS

| | | | |
|---|---|---|---|
| 3,621,198 | 11/1971 | Herbrich | 392/421 |
| 3,636,917 | 1/1972 | Baker | 356/38 |
| 3,717,743 | 2/1973 | Costello | 392/421 |
| 4,233,493 | 11/1980 | Nath | 392/421 |
| 4,789,989 | 12/1988 | Stern | 362/32 |
| 4,956,538 | 9/1990 | Moslehi | 219/405 |
| 5,150,043 | 9/1992 | Flesner | 324/158 R |

FOREIGN PATENT DOCUMENTS

| | | |
|---|---|---|
| 419369 | 3/1991 | European Pat. Off. |
| 475806 | 3/1992 | European Pat. Off. |

OTHER PUBLICATIONS

"Nuclear" solar furnace, Popular Science, Dec. 1958, p. 105.

*Primary Examiner*—Bruce A. Reynolds
*Assistant Examiner*—John A. Jeffery
*Attorney, Agent, or Firm*—John R. Duncan; George T. Parsons

[57] ABSTRACT

An apparatus and method for providing a specified amount of heat on a test specimen, a portion of a specimen, or multiple specimens, under space-like conditions. This system includes a vacuum chamber in which one or more test specimens are placed. This chamber is evacuated to the necessary vacuum. One or more external sources of high intensity light is used for providing the necessary temperature. One or more reflectors are used for concentrating the high intensity light. A fiber optic light guide is used for receiving concentrated light from the reflector. A port in the vacuum chamber wall is used so that the second end of the light guide can extend into the chamber so that light exiting the second end impinges on a selected area of the test specimen. A positioning apparatus is used for locating the second end of the light guide within the housing adjacent to vary the test specimen area subjected to the light. One or more temperature sensors is used on the test specimens for providing feedback to the temperature controlling system for controlling the amount of light input to the guide to achieve the desired temperature.

23 Claims, 4 Drawing Sheets

APPARATUS AND METHOD OF USING FIBER-OPTIC LIGHT GUIDE FOR HEATING ENCLOSED TEST ARTICLES

BACKGROUND OF THE INVENTION

This invention relates to improvements in the apparatus and method for providing specific amounts of heat to a test specimen, and more particularly, but not by way of limitation, to apparatus and method to provide a clean heat source delivering heat with a specified high intensity to induce temperature in the range of over 1000° Fahrenheit (538° Centigrade) to something under 4000° Fahrenheit (2204° Centigrade) when the fiber optic cabling would be destroyed, to one or more test specimens contained within an enclosure, such as a vacuum chamber, for simulating space-like conditions.

Because of the need for ground testing as the most practical and least expensive in simulating space-like conditions, test configurations attempt to simulate the sun which creates a harsh environment through solar flares, storms, and radiation, as well as high intensity heat and light. Ninety percent of the solar energy is distributed in wavelength bands between 276 and 4960 nanometers. Over this region, the sun's spectrum is closely matched by the high-pressure xenon lamp, with the exception of the lamp's strong emission lines in the near-infrared range and some excess ultraviolet. The minimal filtering required and the high efficiency of the xenon lamp mean that both the spectrum and total power of the sun can be achieved in nearly collimated beams over usably-sized areas for laboratory work.

Existing apparatus and methods of heating test specimens do not isolate the heat source outside of the test chamber, nor can the source be readily moved to illuminate various portions of the test article. Existing prior art is complex in design and therefore expensive to build and operate. Other inventions have not eliminated the contamination probability that cannot be tolerated in space simulation testing.

In addition, existing apparatus and methods only partially solve the problems overcome by the present invention. Finally, current known technology has different purposes than the present invention, not just different applications.

The following patents, while of interest in the general field to which the invention pertains, do not disclose the particular aspects of the invention that are of significant interest.

Stern, et al. U.S. Pat. No. 4,789,989, Dec. 6, 1988, shows an apparatus which provides a high intensity light source using a fiber optic light guide into a test chamber, and provides a higher efficiency of power produced by the solar simulator than prior art simulators.

The present invention, by the same inventors, differs from this solar simulator by providing apparatus and a method for cleaner operation for heating one or more test specimens under space-like conditions to a specific temperature, which could exceed that obtained in space by solar illumination alone. However, this simulator describes apparatus to provide light over much of the solar spectrum to only simulate solar illumination levels.

Anderson, et al. U.S. Pat. No. 4,672,199, Jun. 9, 1987 shows an apparatus and method of sensing temperature or pressure, specifically using a light source, a single optical fiber, a measurement system and control circuitry.

This system provides a complex method of sensing temperature, while the present invention provides a more complete system for providing heat to a test specimen under space-like conditions, plus requires only a simple sensing feedback system.

Suga U.S. Pat. No. 4,627,287, Dec. 9, 1986, shows an apparatus for testing specimen surface temperature, specifically using a test chamber, a light source, a sampling mechanism, and a flow divider with air blower.

This tester is structurally complex and focuses on apparatus to maintain a uniform temperature, rather than apparatus and a method to provide a specific amount of heat as the present invention. In addition, this tester is directed to determining resistance to fading in fibers and dyed goods, whereas the present invention is directed toward a method for heating test specimens to a specific temperature.

Numerous other patents have been granted which relate generally to one or more aspects of the present invention. However, all identified prior art is either of more complex design, or involve light properties and applications, instead of heating methods for space based objects. They cannot provide the needed heat in specific locations. Therefore, the present invention is designed for a different capability, is more flexible, and includes a simpler method.

SUMMARY OF THE INVENTION

Briefly stated, the present invention provides a novel apparatus and method for providing a specified amount of heat on test specimens, or a portion of a specimen, under space-like conditions.

This apparatus includes a vacuum chamber containing one or more test specimens, an external source of high intensity light, a fiber optic light guide or guides, means for concentrating and directing the light into a first end of a fiber optic light guide, a port in the chamber through which the second end of the light guide extends, means for directing and concentrating the light exiting the second end onto an area of a test specimen or specimens, means for moving the second end and light directing means to change the area of the specimen receiving the light, and one or more temperature sensors connected to temperature measuring means for controlling the intensity of the light. This temperature measuring means includes a control device and appropriate cables or wiring.

This invention also describes a method of selectively heating test specimens under space-like conditions, includes the steps of providing a housing adapted to contain a test specimen, placing a test specimen in the housing, evacuating the housing to space-like conditions, providing a source of high intensity light, concentrating the light, directing the light into the first end of a fiber optic light guide, locating the second end of the light guide within the housing adjacent to a test specimen or specimen, so that light exiting the second end impinges on a selected area of a test specimen, positioning the second end of the light guide to vary the test specimen area subjected to the light, and controlling the high intensity light using a temperature sensor feedback system to control the amount of light input to the guide to achieve the desired temperature.

The sources of high intensity light could be an arc lamp, concentrated sunlight, or other appropriate light source, or a multiplicity of sources. Several of these sources may be combined to achieve high intensity. An arc lamp is preferable as the source for light input into the fiber optic for several reasons, including high intensity with fairly consistent output, ready availability of both lamps and housings/controllers, and relatively long life, typically 1500 hours.

For focusing a point source onto another point area, an elliptical reflector is the preferred means. If the arc of the light source is carefully placed on one focus of the ellipse, light rays emanating at any angle will be reflected towards the other focus of the ellipse. And a parabolic reflector could also be used alone or in conjunction with other types of reflectors with the sun as the light source. A parabolic reflector can be considered an ellipse with the source focal point essentially at infinity. Such a reflector will focus the near parallel rays from the focal point at infinity, which is fairly well approximated by the sun, onto the focal point of the parabola. A multiplicity of light sources would require multiple reflectors.

The fiber optic light guide needs to be of high transmission efficiency. In a preferred embodiment, the fiber optic guide is made of fused silica cores with silica cladding. The refraction index of the cladding is different from the cores to allow efficient transmission of light. The guide also has minimal hydroxyl content so as to minimize impurities, thereby achieving the lowest reasonable attenuation of light and maximum transmission efficiency of light within the guide. Preferably, for achieving high transmission efficiency, a hydroxyl content of a few parts per million (ppm) is desirable. An example would be an 800 micrometer core diameter fiber with hydroxyl content of less than 2 ppm available from Poly Micro Tech company. This fiber has a very low loss of less than 1 db/km at 1.8 micrometer wavelengths. This construction permits minimal contamination, maximum heat, and maximum efficiency.

The test specimen area subjected to the light could be changed by adjusting the distance to the test specimen from the exit aperture, altering the angle of said light guide in the exit aperture, or changing the area, spot or size illuminated on the test specimen. The preferred alternative would be adjusting the distance to the test specimen because of the ease of physically moving the fiber optic light guide closer to the specimen during initial set up of the system.

Multiple light guides could be used to increase the total area or number of test specimens being illuminated and heated to testing temperatures.

The control mechanism, apparatus, or device which positions the light guide exit aperture with respect to the test specimen could be constructed in several ways, such as a sliding mechanism, spherical bearing, or take up reel. The preferred apparatus is the take up reel because of its range flexibility and simplicity of design.

A feedback mechanism, connecting a controller, multiple temperature sensors, the control mechanism for positioning the light guide exit aperture, and the light source, could be configured in several ways depending on the number of set points and the complexity of temperature profiles provided. One example of a suitable controller would be the Honeywell Corporation model DCP770233 Triple Programmer/controller, which provides a highly flexible unit with multiple control capabilities. Acceptable temperature sensors could be from Omega Engineering, Incorporated. The XCIB series hi-temperature insulated thermocouples are provided in their catalog.

The method is more specifically summarized as follows. A light source, such as OSRAM XBO 2500 high intensity xenon arc lamp, provides light, which is focused, typically using an elliptical reflector toward a light guide. After light enters a fiber-optic light guide, typical of the type of guide used in U.S. Pat. No. 5,013,128, the light is channeled through the guide, which then transmits the light through a port in a vacuum test chamber wall, to the test specimen. The light exiting the light guide heats the test specimen. A controller is used as part of a feedback system to control the amount of light being input to the light guide, thereby achieving the desired temperature. Then a means for controlling the position of the light guide exit aperture with respect to the specimen is provided. This apparatus may also be used for directing the illumination onto the various parts of the specimen, in order to heat different areas for predetermined lengths of time, or for controlling the distance to the specimen, which would, in turn, change the spot size illuminated, and the resulting flux.

This method distinguishes the present invention from prior art since previous methods do not address the entire system of providing specific amounts of heat in a space-like environment.

Problems overcome by this invention include: 1) the expense of previous methods, 2) elimination of outgassing and contamination, which may be byproducts of conventional heat sources, and 3) needing large vacuum chamber ports or windows to transmit light directly without using a light guide.

The present invention provides a simple and flexible method which, in a direct, and clean way, provides heat to a test specimen. Advantages of the present invention include the use of a fiber-optic light guide to take high intensity light from an arc lamp or other appropriate source, and transmit it to the specimen within the test chamber. The use of a light guide physically separates the thermal source from the test chamber, eliminating the problems with outgassing, contamination and potential failures of heating elements normally used within the test chamber. A second advantage is in the ability to easily change the areas being heated, and the flux upon these areas, by changing the location of the exit aperture of the light guide with respect to the specimen. Thirdly, this approach has the advantage of eliminating ignition sources, such as electrical wiring leading to quartz heaters often used in typical vacuum chambers.

These and other aspects of the present invention are set forth more completely in the accompanying figures and the following description.

DETAILED DESCRIPTION OF PREFERRED EMBODIMENTS

Figure 1:
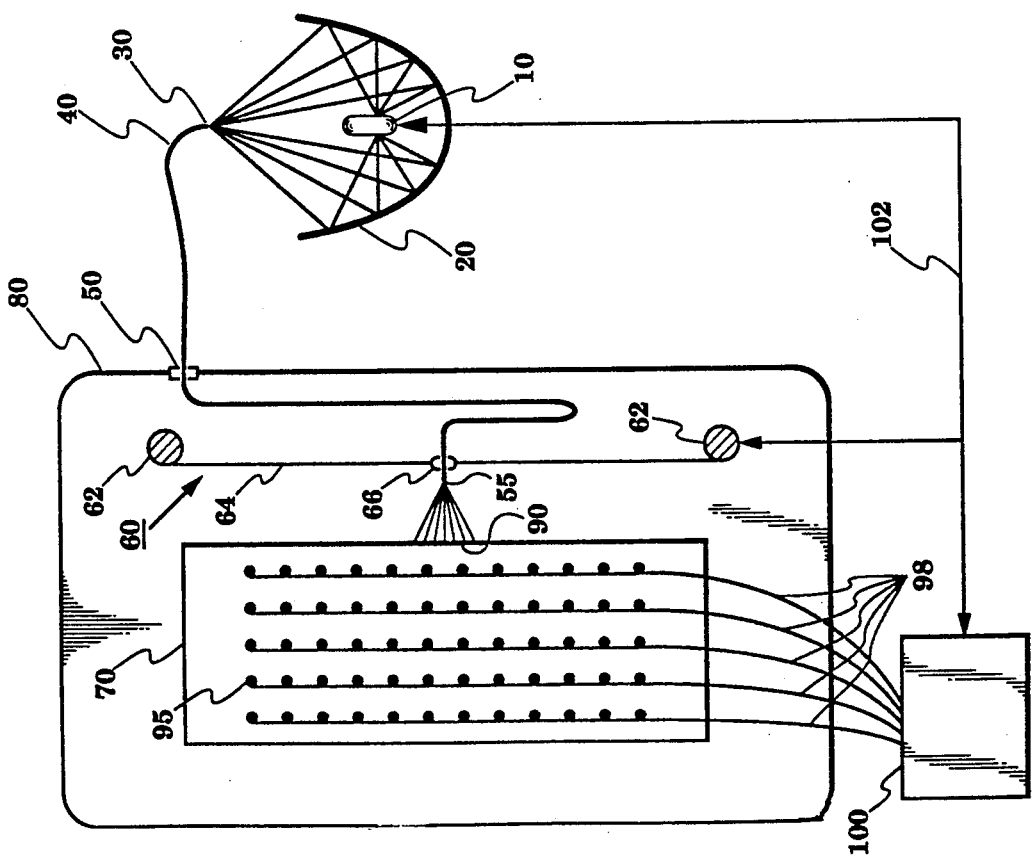
FIG. 1 is a schematic showing a first embodiment of apparatus for providing heat onto a test specimen in accordance with the present invention.

Referring to FIG. 1, there is seen an electric arc energy source 10 at one focus of a reflector 20. This reflector could be an elliptically shaped one or parabolic shaped one, or multiple reflectors of the same or dissimilar types, depending on the different high intensity light sources. A light guide entrance aperture is at the other focus 30. A fiber optic light guide 40 leads from the reflector 20 to a port 50 in the wall of the vacuum chamber 80. This fiber optic light guide 40 is of high transmission efficiency made of fused silica cores with silica cladding, with the silica cladding having a different refraction index from the silica cores to allow sufficient reflection within the fiber optic guide 40. The fiber optic guide 40 also has minimal hydroxl content so as to achieve a low attenuation of light within the guide 40. The minimum hydroxl content preferably would be on the order of less than 2 ppm. This construction permits minimal contamination, maximum heat, and maximum efficiency.

The port 50 provides the path for the fiber optic guide 40 into the test chamber 80. There could be multiple ports depending on the number of light guides required. This port 50 is constructed to hold a vacuum in the test chamber 80. Apparatus for positioning of the light guide 40 is a take up reel system 60, including the following components or subsystems: multiple take up reels 62, take up reel roll apparatus 64, and aperture 66 which is within the take up reel roll apparatus 64. The test specimen 70 can be one or more specimens depending on the test procedures. An area 90 of the specimen is heated by the light exiting the light guide exit aperture 55 from the fiber optic light guide 40. Temperature sensors 95 are placed inside the vacuum chamber 80 and attached to the test specimen 70 or specimens as called out in the test procedures. These sensors 95 monitor the temperatures resulting from high intensity light on the test specimen 70. A multiplicity of wires or cables 98 connect from the temperature sensors 95 to the feedback control device 100. This device 100 controls the amount of light from the light source 10 to achieve the desired test temperature. Other cabling or wiring 102 connect the feedback control device 100 to the one or more heat sources 10.

Figure 2:
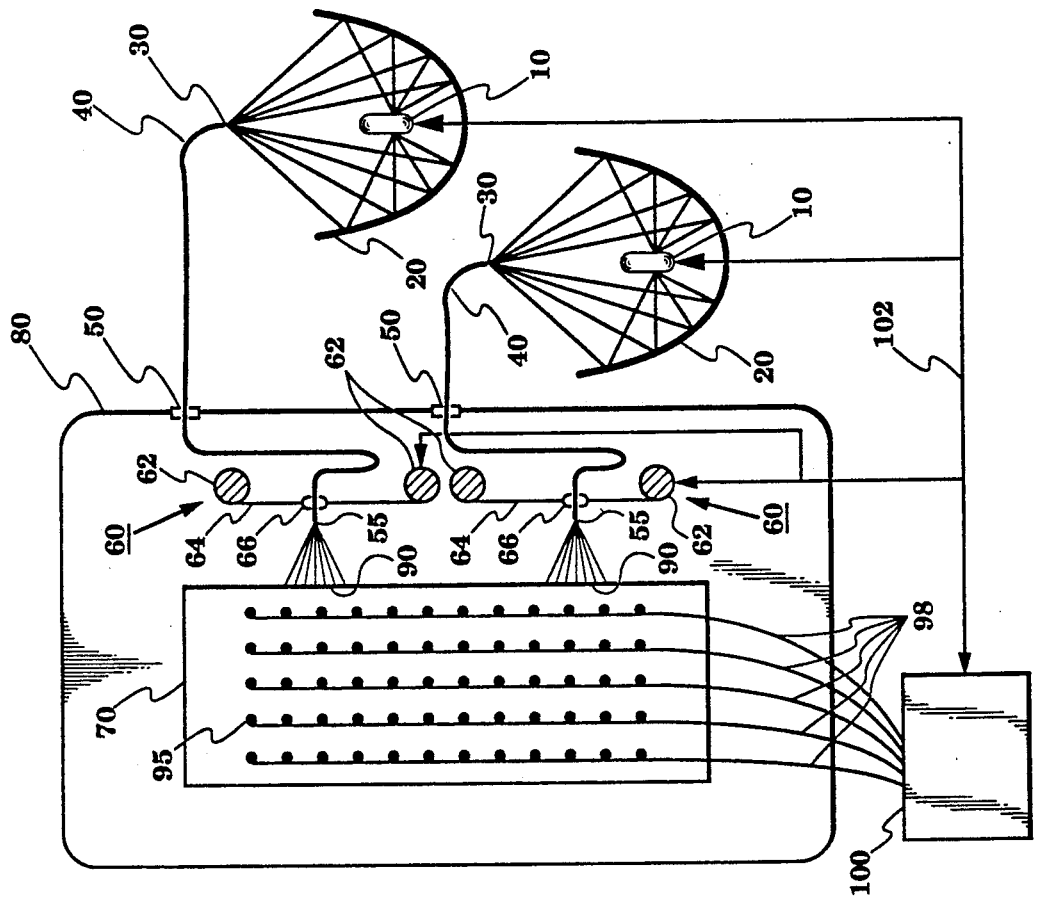
FIG. 2 is a detail schematic showing of a second embodiment of the appartus of FIG. 1, having multiple sources of light.

Referring to FIG. 2, the source of high intensity light is shown from a multiplicity of sources, such as duplicating the elliptical shaped reflector from FIG. 1 as shown, or using a parabolic shaped reflector, or other appropriate means for focusing the high intensity light.

Figure 3:
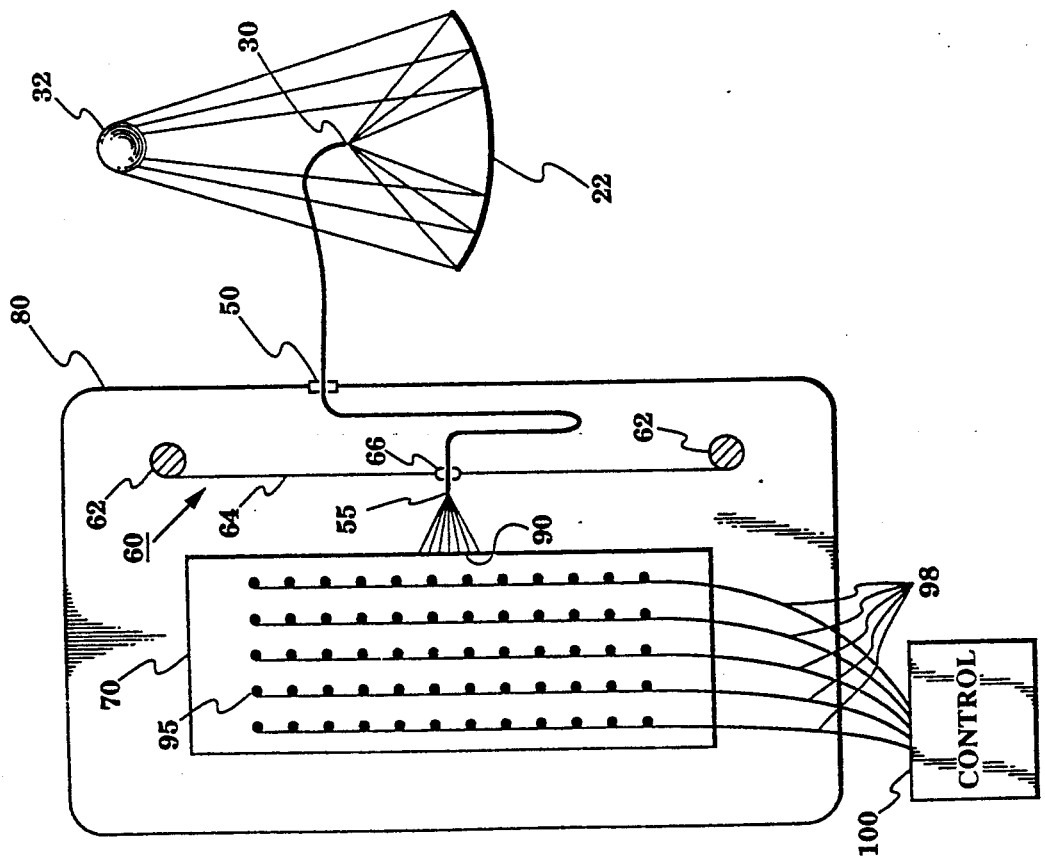
FIG. 3 is a detail schematic showing of a third embodiment of the apparatus of FIG. 1, having sunlight as the light source, and using a parabolic reflector.

Referring to FIG. 3, the source of high intensity light is shown as concentrated sunlight 32, with a parabolic shaped reflector 22.

Figure 4:
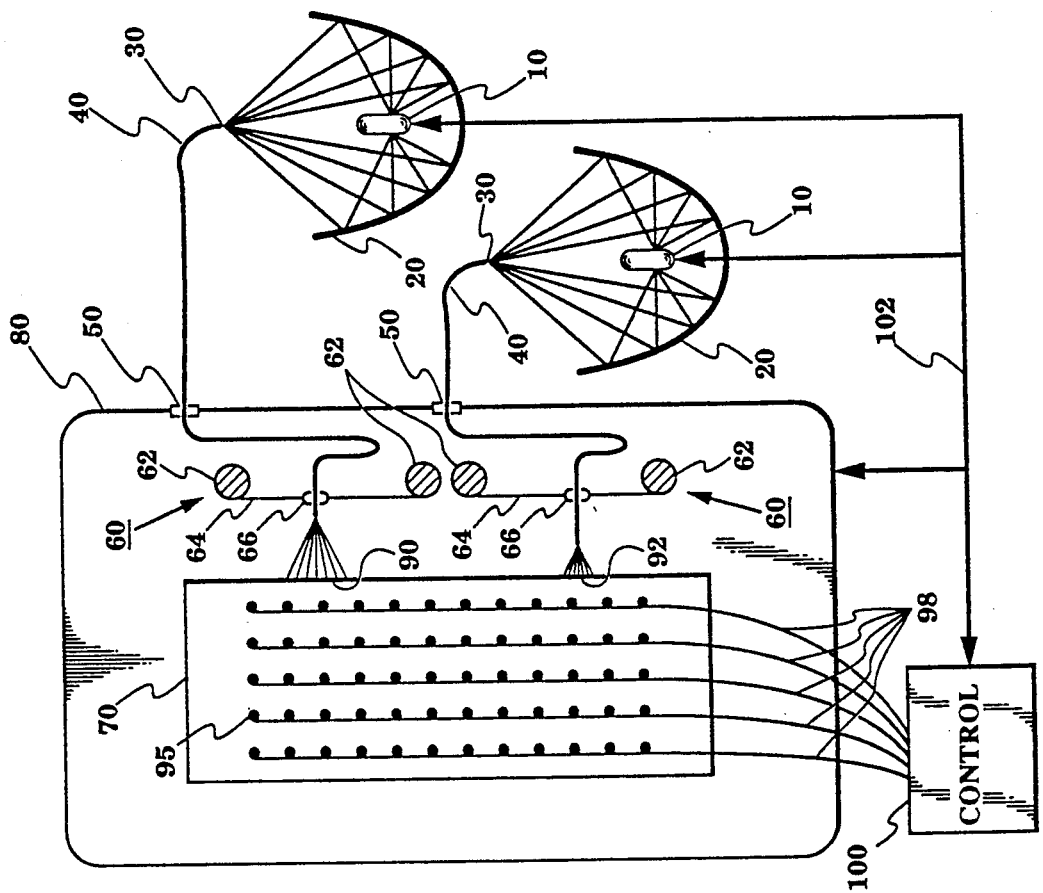
FIG. 4 is a detail schematic showing of a fourth embodiment of the apparatus of FIG. 1, having a smaller area of the test specimen heated, using a longer length of fiber optic light guide.

Referring to FIG. 4, the positioning apparatus 60 and the fiber optic guide 40 can be adjusted so that the distance is less between the exit aperture 55 and the test specimen 70 in order to illuminate a smaller portion 92 of the test specimen 70.

Figure 5:
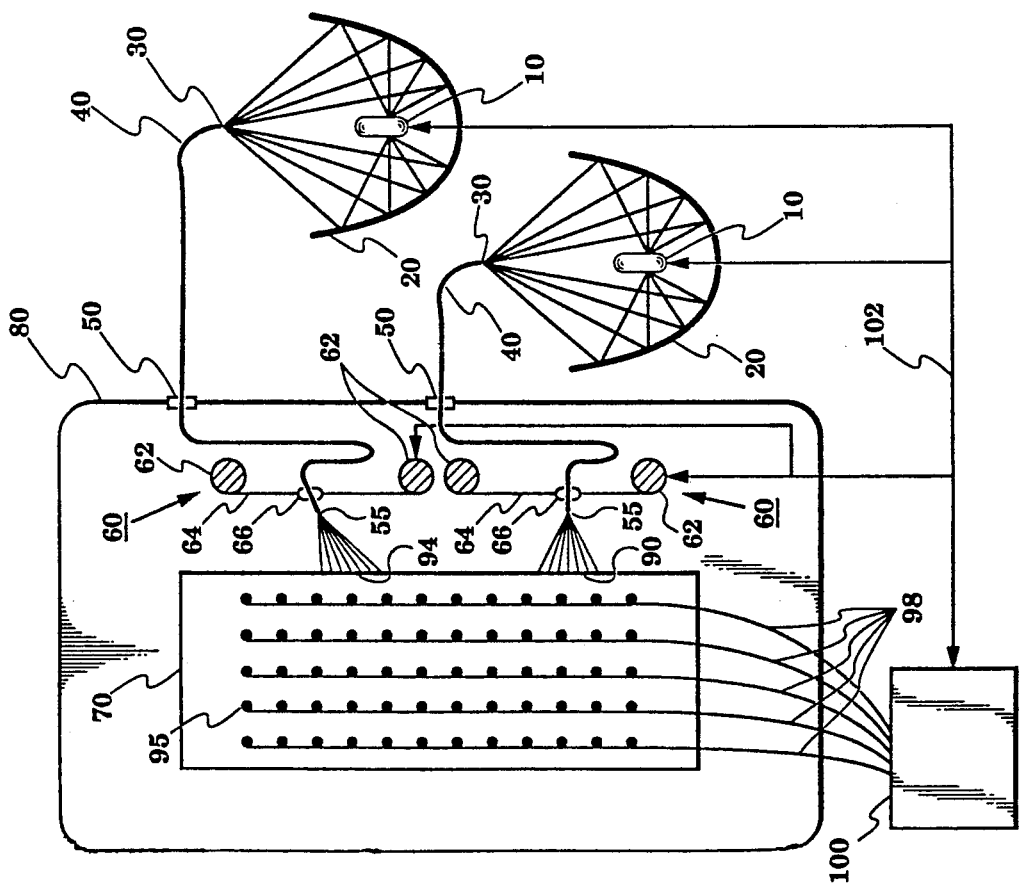
FIG. 5 is a detail schematic showing of a fifth embodiment of the apparatus of FIG. 1, having an altered angle of the fiber optic light guide which provides heating to a different area of the test specimen.

Referring to FIG. 5, the amount of light is changed by altering the angle of the light guide 40 and the exit aperture 55, by use of a typical spherical bearing and a typical associated mechanism in the take up roll, to cover a different area 94 of the test specimen 70.

Figure 6:
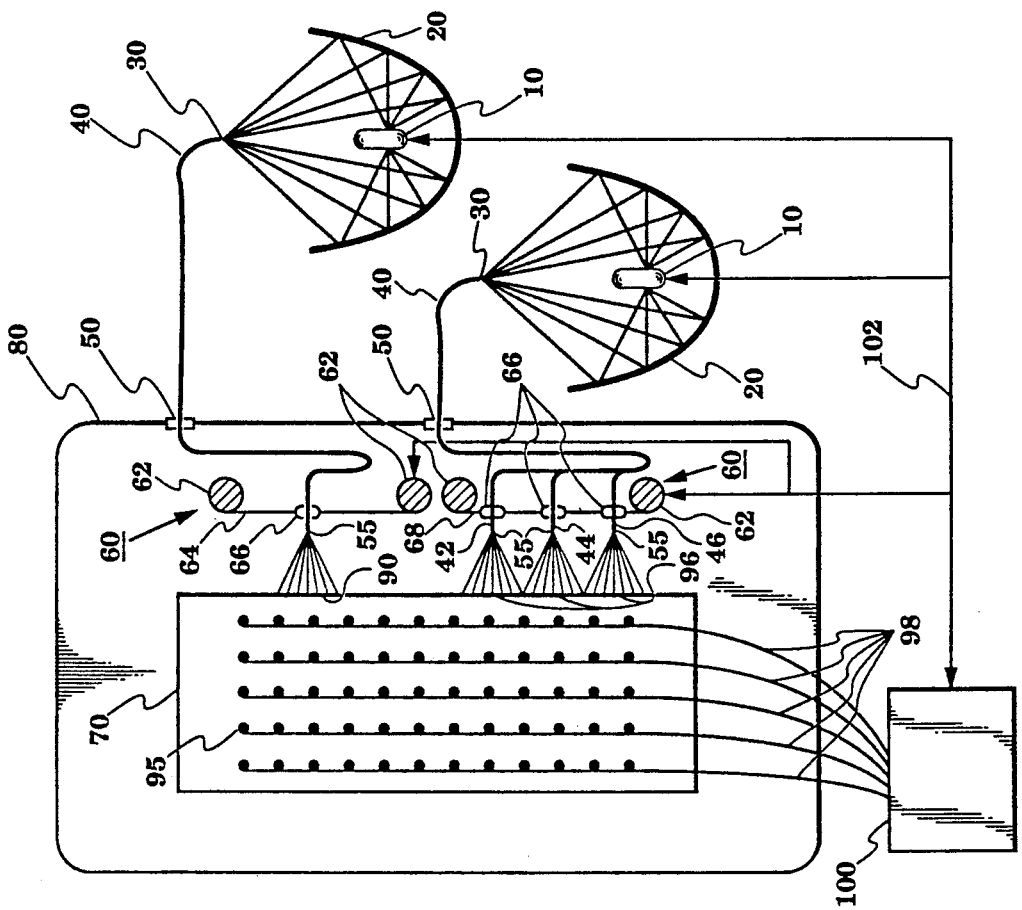
FIG. 6 is a detail schematic showing of a sixth embodiment of the apparatus of FIG. 1, having a fiber optic light guide which is split into three guides within the vacuum chamber, and thereby heating a wider area of the test specimen.

Referring to FIG. 6, the area 96 of the test specimen illuminated is shown in still another configuration by splitting the fiber optic guide 40 into three strands, 42, 44, and 46. These strands go through the take up roll 68, modified from the previously mentioned roll 64 in FIG. 1, which has just one aperture 66.

Figure 7:
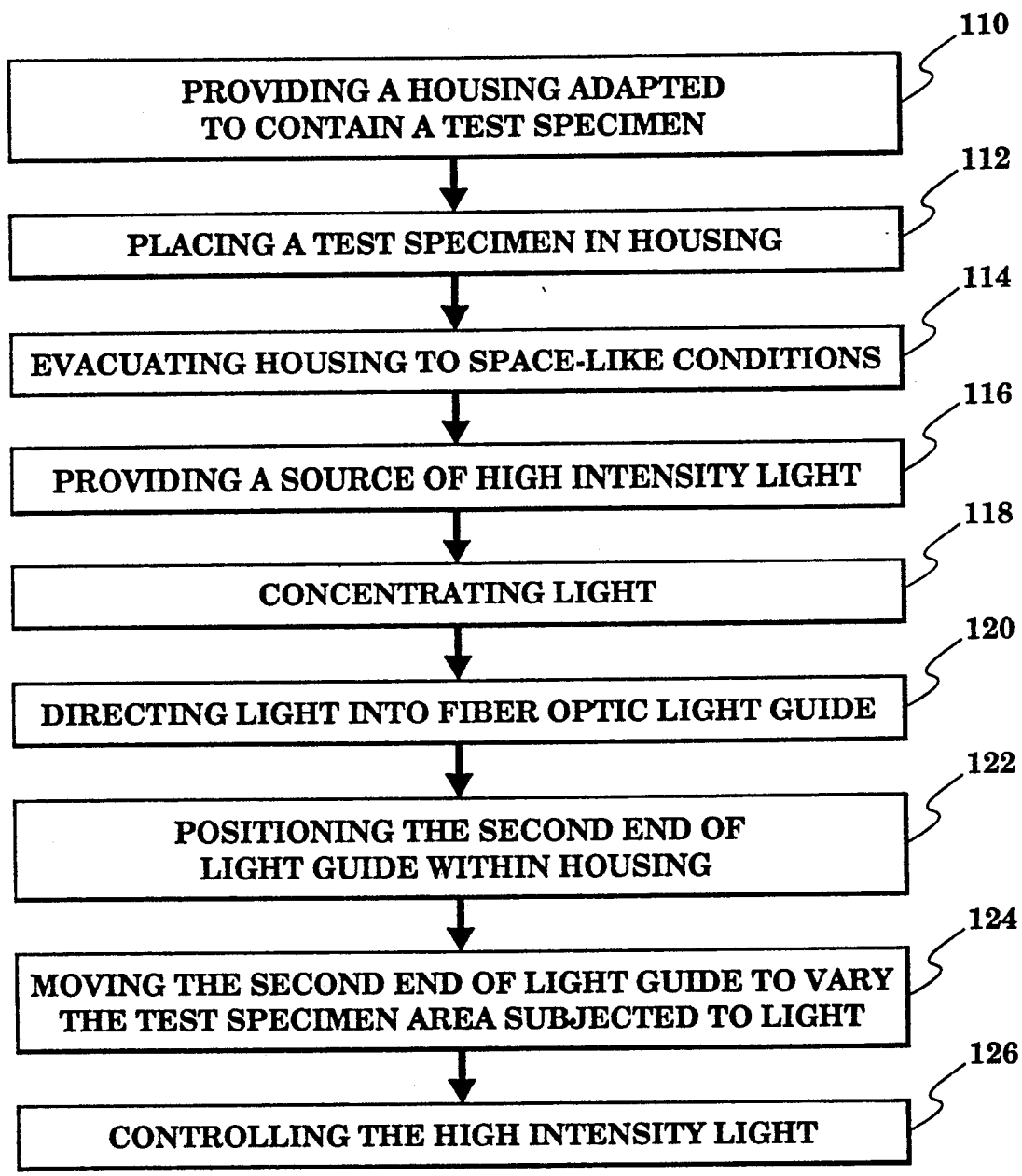
FIG. 7 is a block diagram illustrating the method of heating test specimens within a vacuum chamber.

The method of this invention is substantially illustrated by the block diagram of FIG. 7, which points out the basic steps of operation.

The first step, as indicated in box 110, is providing a housing adapted to contain a test specimen.

The second step, as indicated in box 112, is placing a test specimen in the housing.

Then the next step, as indicated in box 114, is evacuating the housing to space-like conditions, using any conventional vacuum pump. The proposed system is applicable to a wide variety of test conditions. Typical pressure for a space simulation test is about 10-6 torr, which simulates pressure in low earth orbit. However, other test conditions could be used depending on the test objectives. The use of inert atmospheres of argon or nitrogen is also a potential candidate for testing certain items.

The next step, as indicated in box 116, is providing high intensity light from a source.

The next step, as indicated in box 118, is concentrating the light by using a device such as an elliptically shaped reflector 20, or other concentrating means.

The next step, as indicated in box 120, is directing the light into the first end of a fiber optic light guide, such as a light guide entrance aperture 30.

The next step, as indicated in box 122, is positioning the second end of the light guide within the housing adjacent to the test specimen, so that light exiting the second end impinges on a selected area of the test specimen.

The next step, as indicated in box 124, is moving the second end of the light guide to vary the test speciment area subjected to the light. This moving can be accomplished in one of several means: adjusting the distance of the fiber optic light guide 40 to the test specimen 70, moving the take up reel roll 64 parallel to the specimen 70 through mechanical means, or adjusting the angle of the light guide 40 in the exit aperture 55 by use of a conventional spherical bearing.

The last step, as indicated in box 126, is controlling the high intensity light by using a temperature sensor feedback system to control the amount of light input to the guide to achieve the desired temperature.

It can be seen that the present invention provides a simple, safe, clean, and inexpensive method which provides specific amounts of heat on specific test articles to simulate space-like conditions.

The foregoing description of the invention is explanatory thereof and various changes in the size, shape and materials, as well as on the details of the illustrated construction may be made, within the scope of the appended claims without departing from the spirit of the invention.

What is claimed is:

1. An apparatus for selectively heating test specimens in a space-like atmosphere, which comprises:

a vacuum chamber adapted to contain a test specimen;

a source of high intensity light;

a fiber optic light guide;

means for concentrating and directing said light emitted by said source into a first end of said fiber optic light guide;

a port in said chamber through which said light guide extends;

means for directing light exiting a second end of said light guide onto an area of a test specimen within said chamber;

take up roll means for moving said second end and said light directing means along a path substantially parallel to said specimen to change the area of said specimen receiving said light; and temperature measuring means for controlling the intensity of said light.

2. The apparatus according to claim 1, wherein the said source of high intensity light is an arc lamp.

3. The apparatus according to claim 1, wherein the said source of high intensity light is concentrated sunlight.

4. The apparatus according to claim 1, wherein the said source of high intensity light includes a multiplicity of light sources.

5. The apparatus according to claim 1, wherein the said fiber optic light guide includes a multiplicity of said guides.

6. The apparatus according to claim 1, wherein the means for concentrating and directing said light into said first end of said fiber optic light guide is an elliptically shaped reflector.

7. The apparatus according to claim 1, wherein the means for concentrating and directing said light into said first end of said fiber optic light guide is a multiplicity of elliptically shaped reflectors.

8. The apparatus according to claim 1, wherein the means for concentrating and directing said light into said first end of said fiber optic light guide is a parabolic shaped reflector.

9. The apparatus according to claim 1, wherein the means for changing the area of said specimen receiving said light is a mechanism for mechanically adjusting the distance to said test specimen.

10. The apparatus according to claim 1, wherein the means for changing the area of said specimen receiving said light further includes a mechanism for adjusting the angle of said light guide in an aperture through mechanical means, including a spherical bearing device in said aperture of said take up reel roll.

11. The apparatus according to claim 1, wherein the means for changing the area of said specimen receiving said light is a multiplicity of guides split from said light guide extending through said take up reel roll through separate said apertures in said roll.

12. The apparatus according to claim 1 wherein said fiber optic guide comprises fused silica cores with silica cladding of a different refraction index from the silica cladding, with minimal hydroxl content so as to achieve a low attenuation of light within said guide.

13. The apparatus according to claim 12 wherein said fiber optic guide contains a minimum hydroxl content of about less than 2 ppm, so as to achieve a low attenuation of light within said guide.

14. The apparatus according to claim 1 wherein the temperature measuring means for controlling the intensity of said light is a control device adapted for the number of required data points.

15. An improved method of selectively heating test specimens under space-like conditions, comprising the steps of:

providing a housing adapted to contain a test specimen;

placing said test specimen in said housing;

evacuating said housing to space-like conditions;

providing a high intensity light;

concentrating light from a source;

directing said light into a first end of a fiber optic light guide having first and second ends;

positioning the second end of said light guide within said housing on a take up reel roll adjacent to said test specimen, so that light exiting said second end impinges on a selected area of said test specimen;

changing the angle of said second end of said light guide relative to the surface of said specimen to vary said test specimen area subjected to said light; and controlling said high intensity light using a temperature sensor feedback system to control the amount of light input to said guide to achieve the desired temperature.

16. The method according to claim 15 wherein the amount of light input is controlled to heat said area to a temperature from about 1000° to 4000° Fahrenheit.

17. The method according to claim 15 including directing said light into a plurality of fiber optic light guides to increase the area of said test specimen being heated.

18. The method according to claim 15 wherein said housing is evacuated to space-like conditions by connecting a conventional vacuum pump inserted into said vacuum chamber.

19. The method according to claim 15 wherein said light source provides a high intensity light from a mounting outside said vacuum chamber.

20. The method according to claim 15 wherein said source is concentrating light by reflecting said light from said elliptical reflector.

21. The method according to claim 15 wherein said second end of said light guide within said housing is positioned to vary said test specimen area subjected to said light by physically moving said fiber optic guide closer to said test specimen.

22. The method according to claim 15 wherein said second end of said light guide within said housing is moved to vary said test specimen area subjected to said light by moving said take up reel roll parallel to said test specimen.

23. The method according to claim 15 wherein controlling said high intensity light uses a temperature sensor feedback system to control the amount of light input to said guide to achieve the desired temperature.

* * * * *